United States Patent [19]
Bao

[11] Patent Number: 5,522,898
[45] Date of Patent: Jun. 4, 1996

[54] DEHYDRATION OF HYDROGELS

[75] Inventor: Qi-Bin Bao, Livingston, N.J.

[73] Assignee: Howmedica Inc., New York, N.Y.

[21] Appl. No.: 122,110

[22] Filed: Sep. 16, 1993

[51] Int. Cl.$^6$ .................................. A61F 2/44; F26B 3/00
[52] U.S. Cl. ............................. 623/17; 623/11; 623/901; 264/340; 264/344; 34/475; 236/44 C
[58] Field of Search .............................. 623/4, 5, 11, 16, 623/17, 901; 34/443, 474, 475; 236/44 C; 264/344, 340

[56] References Cited

U.S. PATENT DOCUMENTS

| | | | |
|---|---|---|---|
| 3,234,659 | 2/1966 | Smith | 34/475 |
| 3,760,045 | 9/1973 | Thiele et al. | 264/1 |
| 4,663,358 | 5/1987 | Hyoa et al. | |
| 4,808,353 | 2/1989 | Mambu et al. | |
| 5,012,503 | 4/1991 | Mambu et al. | |
| 5,047,055 | 9/1991 | Bao | 623/17 |
| 5,314,478 | 5/1994 | Oka et al. | 623/18 |

OTHER PUBLICATIONS

Journal of Applied Polymer Science; Y. T. Shah and J. H. Porter, vol. 17, pp. 605–618 (1973).
European Polymer Journal; N. A. Peppas, vol. 12, pp. 495 to 498, Pergamon Press, 1976.

*Primary Examiner*—David Isabella
*Assistant Examiner*—Laura Fossum
*Attorney, Agent, or Firm*—Peter C. Richardson; Lawrence C. Akers; Elizabeth O. Slade

[57] ABSTRACT

Novel prosthetic nuclear implants for insertion into vertebral discs are prepared by dehydrating hydrated bulky hydrogel discs under specific conditions so as to reduce the water content as low as possible (down to about 10% by weight) but without distortion of the implants, without the formation of concavities and sharp edges, and without changing the shape of the hydrated implant.

9 Claims, 3 Drawing Sheets

DEHYDRATION OF HYDROGELS

FIELD OF THE INVENTION

This invention relates to bulky hydrogels and relates in particular to a method of preparation of prosthetic nuclei for vertebral discs.

BACKGROUND OF THE INVENTION

An important area of research in the field of medical devices is the development of a prosthetic nucleus for a vertebral disc. In U.S. Pat. No. 5,047,055, a prosthetic nucleus for implanting in the disc space after the removal of a degenerated or damaged nucleus of an intervertebral disc is disclosed and claimed, as well as a method for forming the prosthetic nucleus. That patent is hereby incorporated herein by reference.

In making such a prosthetic nucleus for insertion, the implants made of bulky hydrogels should be dehydrated so that they have a water content as low as possible. This allows for easy insertion of the disc component during surgery due to the accompanying reduction in volume. Additionally, it is desirable for the implant to have no distortions (i.e., no concavities or dimplings formed therein) and it is desirable that the apparent volume (defined herein to be the volume that the disc would have if it had no concavities and is equal to the largest cross-section of the disc multiplied by the largest disc width) of the implant be a minimum. Furthermore, it is desirable that the implant have no sharp edges. It is especially important to have a minimum dehydrated volume for an implant which is to be inserted percutaneously.

However, it has been found that when the bulky hydrogels as disclosed in U.S. Pat. No. 5,047,055 are dehydrated so as to reduce the water content as low as possible, under certain conditions, gross distortions of the implants occur. These distortions may not be acceptable in the intended medical application. For example, sharp edges on the superior and inferior surfaces of the implants can cause damage on the end-plates of the natural disc.

It is an object of this invention to produce vertebral disc implants which have a water content as low as possible, which exhibit (to the naked eye) no visible distortion of the implants and no sharp edges, and which have a minimum apparent volume.

Another object of this invention is a method of dehydration of a bulky hydrogel implant so as to maintain the original shape of the hydrated implant.

Yet another object of this invention is an implant having a water content which is as low as possible (i.e., below about 10%) and which has a minimal apparent volume, no sharp edges, and no visible distortion (that is, no visible concavities) in the implant.

Yet another object of this invention is to dehydrate vertebral disc implants to a consistent geometry and size.

SUMMARY OF THE INVENTION

These and other objects of the invention are satisfied by the method of the invention for dehydration of bulky hydrogel nuclear vertebral implants which are of a size weighing between about 3 and about 10 grams and of a shape which is substantially in the shape of a kidney (that is, a shape similar to that of a human vertebral disc nucleus) comprising dehydrating these implants under controlled conditions of relative humidity and temperature and time such that when the water content of these implants is within a critical range of about 30 to about 60% by weight, the samples dry so that they avoid the formation of any cavities. Above a water content of about 60 weight percent and below about 30 weight percent water content, the dehydration appears to be not so critical and the dehydration can proceed without distortions, under ambient conditions. Unexpectedly, it has been found that for these implants of the specific size (most preferably about 5 grams), kidney shape, and specific materials (bulky hydrogels as set out fully in U.S. Pat. No. 5,047,055 and described below), the conditions for drying are critical for the water content range of about 30–60% and should be (a) relative humidity of at least about 80%, preferably in the range from about 90 to about 99%, and most preferably at least 95%, (b) a drying temperature within the range from about 10° to about 40° C. and preferably about room temperature to about 35° C., and (c) a time of drying sufficient to enable the samples to be dried without distortion to a water content below about 30% and preferably to about 10%, the time being generally several days.

Such implants when dehydrated according to the method of the invention exhibit an apparent volume which is a minimum, no sharp edges, and no visible distortions (i.e., no concavity) in the implant. When the conditions used in the method of the invention are not used for dehydrating the implants in the critical range, the resultant implants have visible distortions, have sharp edges, and do not have an apparent volume which is minimal.

Also according to the invention, a bulky hydrogel implant suitable for implantation as an artificial nucleus in a vertebral disc has a water content less than about 30 weight percent, has no visible distortions, has no sharp edges, has a dehydrated weight within the range from about 0.5 g. to about 3.0 g. and has a shape which is substantially in the shape of a kidney.

DESCRIPTION OF THE PREFERRED EMBODIMENTS DESCRIPTION OF THE DRAWINGS

FIG. 1 is a set of three graphs of water content (in percentage of water by weight) plotted versus time of dehydration (in days) of three samples of hydrogels (further described herein and in U.S. Pat. No. 5,047,055, which has been incorporated herein by reference). Graphs A and B are for controls and Graph C is for an implant of the invention dehydrated according to the method of the invention, using in this case a humidity chamber with a relative humidity of 98% and a temperature of 35° C. Graphs 1A and 1B are described in Example 1 and Graph 1C is described in Example 2 (given below).

Figure 4:
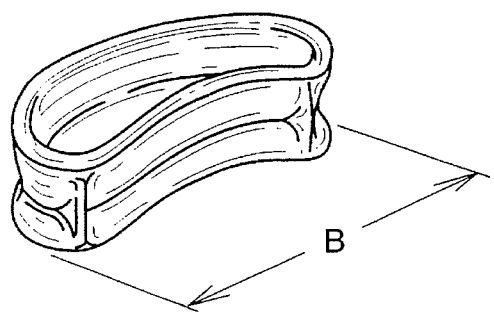

FIG. 4 is an enlarged drawing of a dehydrated vertebral nucleus implant. The implant was dehydrated under ambient conditions. The distortion concavity surfaces and sharp edges at the corners are visible. The length B is the width.

Figure 5:
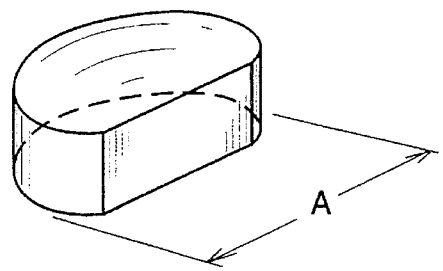

FIG. 5 is an enlarged drawing of a dehydrated vertebral nucleus implant of the invention which was dehydrated under the controlled conditions as described in Example 2. There is no visible distortion, concavity, or sharp edges. The length A is the width. The apparent volume of the implant in FIG. 5 is smaller than that in FIG. 4, and width B is larger than width A.

Figure 3:
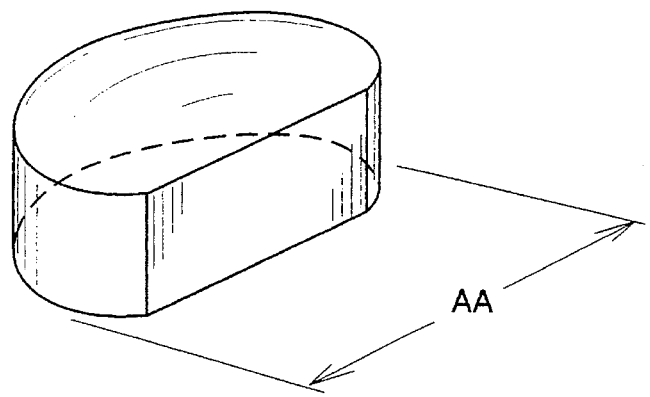
FIG. 3 is an enlarged drawing of a fully hydrated hydrogel vertebral nucleus implant of kidney shape before dehydration. The length AA is the width of the implant.

FIGS. 3, 4 and 5 are drawn to the same scale.

The particular materials which are used for the synthetic vertebral nuclear disc implants are fully described and set out in U.S. Pat. No. 5,047,055, which has been incorporated herein by reference. As set out in that patent, the preferred material of the implants is a hydrogel material, preferably highly hydrolyzed polyvinyl alcohol (PVA). The mount of hydrolization may be between about 95 and 100%, depending on the preferred final water content desired, which is about 70 to about 90 weight percent. Generally the final hydrogel water content increases as the percent of hydrolization of the initial PVA decreases.

The method of preparing the prosthetic nucleus implants is fully set forth in U.S. Pat. No. 5,047,055. Also as disclosed in that patent, other hydrogels (besides preferred PVA) which can be used in the synthetic nucleus implants include other hydrogels such as lightly cross-linked polymers of 2-hydroxyethyl methacrylate, or copolymers and terpolymers made from the combination of the monomers of an N-vinyl monomer, (for example, N-vinyl-2-pyrrolidone(N-VP)), a hydroxy alkyl methacrylate ester (for example, 2-hydroxyethyl methacrylate (HEMA)), an alkyl methacrylate (for example, methyl methacrylate (MMA), an ethylenically unsaturated acid (for example, methacrylic acid (MA)) and an ethylenically unsaturated base (for example N,N-diethylamino ethyl methacrylate (DEAEMA)) may be used. In general, any hydrogel that can be used for soft contact lenses can be used for the synthetic nucleus implants as long as the hydrogel exhibits a compressive strength of at least 4 $MNm^{-2}$.

The size of the implants will generally be within the range of from about 3 to about 10 grams before dehydration, and preferably will be about 5 grams before dehydration.

The shape of the synthetic nuclear disc implants will be substantially in the shape of a kidney or any shape similar to the shape of a human vertebral disc nucleus.

The relative humidity suitable for use in the method of dehydrating the implants is a relative humidity in the atmosphere of at least 80% and preferably within the range from about 90 to 99% and most preferably above 98%.

The temperature to be used in the dehydration method should be within the range from about 10° to about 40° C. and preferably will be within the range from about 20° to about 35° C. The higher the temperature, the faster the water within the hydrated implants will diffuse to the surface of the implants.

It has been found that for the bulky hydrogels used in the implants, for the size of the implants, and for the shape of the implants, it is very important (if not critical) that when the water content of the implants is between about 30 and about 60 weight percent, the implants should be dehydrated with the humidity being controlled within the ranges as described above, and at the temperatures as described above, and for a length of time which is quite long so as to avoid deformation of the implants when they are being dehydrated. When the relative humidity is lowered, the time of dehydration can also be lowered. However, to provide good results, the time of drying will generally be at least several days (i.e., more than two but fewer than many).

EXAMPLE 1

(Control)

A hydrogel prosthetic nucleus implant starting with a wet weight about 5 grams and with a water content of about 85% was dehydrated under conditions of ambient temperature and humidity. Although the laboratory has air conditioning, the relative humidity was in the range of about 45% to about 85% during the period of the dehydration. The relative humidity each day during the dehydration period was recorded, and the averages are labeled in the plot. The room temperature was relatively stable (between 20°–22° C.). The high relative humidity (above 75%) in the first two days made this dehydration very slow during this period. The weight of the implant was monitored over the dehydration period, and the water content of the implant vs. the time is plotted in FIG. 1 (curve A). The shape of the implant was also monitored visually over time. In the early dehydration period when the implant still had high water content (wherein the water content was between about 85% to about 65%), the implant maintained its original shape without distortion even though the water content (and thus the weight) of the implant decreased relatively quickly. In this range of water content, the implant remained very soft to the touch. As dehydration continued, the implant surfaces started to become rigid; and concavities became visible on the surfaces when the implant had a water content of about 50%. The concavities increased as the water content decreased further.

Figure 1:
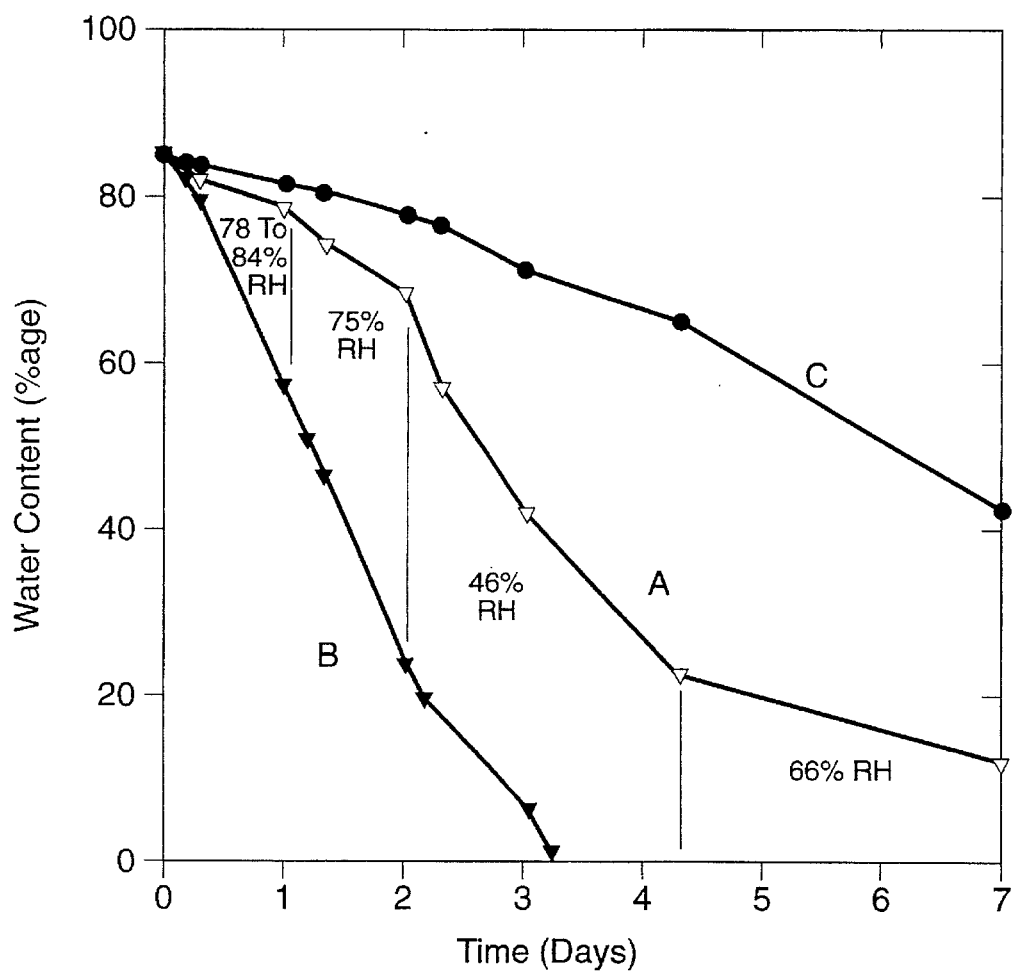
Figure 2:
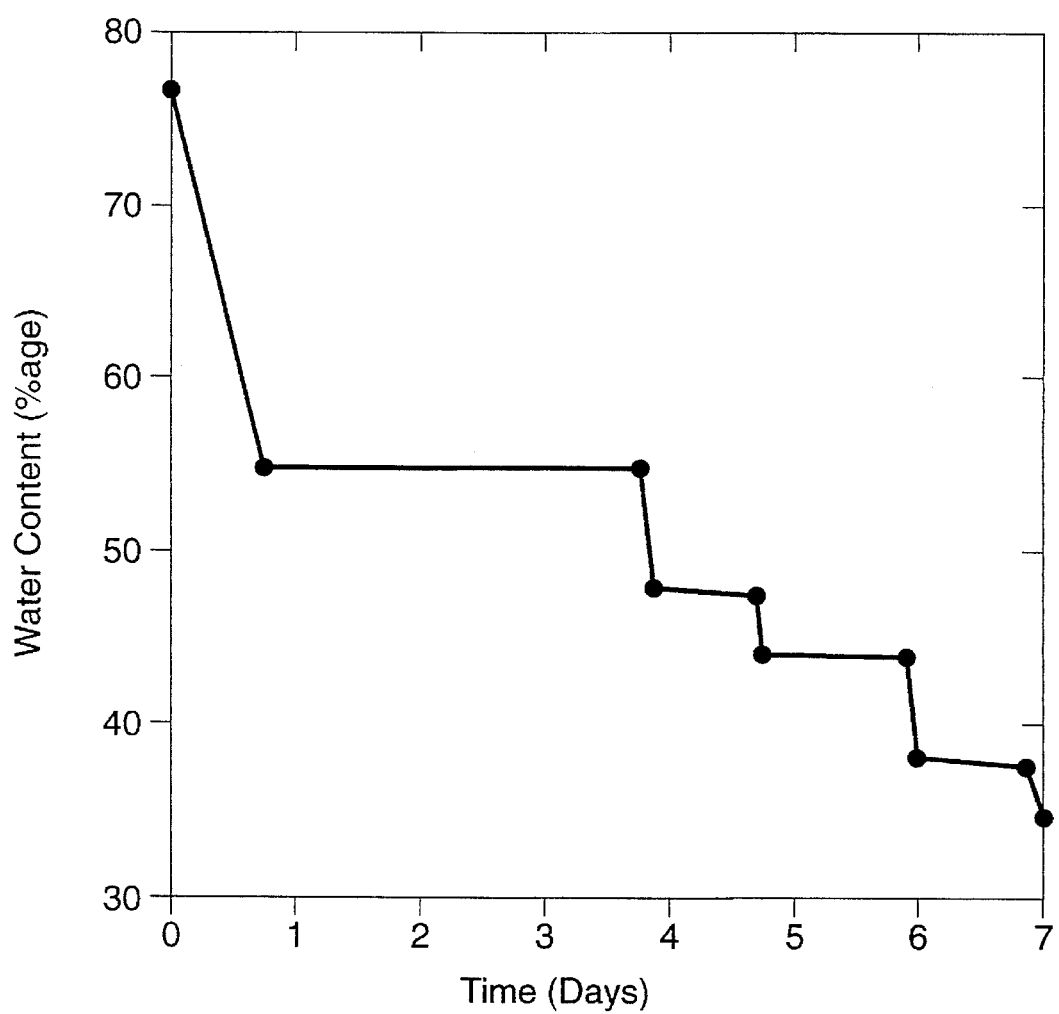
FIG. 2 is a graph of water content versus time (in days) for an implant of the invention (dehydrated so that it has no distortions therein, no sharp edges, and a minimal apparent volume, formed as described in Example 3 by dehydrating the implant within a container which is alternately uncovered and then closed.

In FIG. 1, curve B is the dehydration of a substantially similar implant dehydrated with low relative humidity (about 60%) in the same laboratory. Again, concavities formed.

EXAMPLE 2

(Invention)

A similar size hydrogel nucleus implant as was used as starting material in Example 1 was dehydrated in a Temperature/Humidity controlled chamber, called a TH Jr. (and manufactured by Tenny Engineering, Inc., Union, N.J.) at 35° C. and at a relative humidity of 98%. The weight and the shape of the implant were checked over time. Water content vs. time is plotted in FIG. 1, curve C. It can be seen that the dehydration rate was substantially decreased at high humidity, as compared with the rate of low humidity. The implant kept its original shape without the formation of any visible concavities even when the water content dropped to about 25%.

Next, the implant was dried further in a vacuum oven at 35° C. This further dehydration did not result in any visible concavity formation (as viewed by the naked eye).

EXAMPLE 3

(Invention)

In this example, a hydrogel implant as was used as starting material in Example 1 but with a water content of about 77% was first allowed to dehydrate quickly in air until the water content was about 54%. This occurred over about one day, and the relative humidity of the air was between 20–40%. Then, the implant was kept in a small closed container for the next three days. Then the implant was exposed to air again (with a relative humidity of 20–40% for a period of about one day) and more water evaporated. Next, the hydrogel implant was placed in the container again. These steps were repeated until the water content of the implant was about 30%. Then the implant was allowed to dehydrate further under vacuum. (This further dehydration could have been done alternatively in air but for a longer period of time.) The implant dehydrated in this way provided a dehydrated implant (with water content of less than 10 weight %) with no concavity on the surfaces.

I claim:

1. A method of dehydrating a bulky hydrogel nuclear vertebral implant having a weight before dehydration between about 3 and about 10 grams and having a shape substantially similar to a human vertebral disc nucleus and having a water content before dehydration between about 30 and about 60% by weight, said method comprising: dehydrating said implant at (a) a relative humidity of at least about 80%, (b) at a drying temperature between about 10° and about 40° C., and (c) for a time of drying of more than two days.

2. A method according to claim 1, wherein said implant weighs about 5 grams before dehydration, is made of bulky hydrogel material comprising highly hydrolyzed polyvinyl alcohol and said hydrogel exhibiting a compressive strength of at least 4 MNm$^{-2}$, wherein said relative humidity is within a range from about 90 to about 99% and wherein said drying temperature is within a range from about 20° to about 35° C.

3. A method according to claim 2, wherein said relative humidity is at least about 95% and wherein said dehydration takes place within a humidity chamber.

4. A method of dehydration of a hydrated bulky hydrogel implant having an original shape, said hydrogel being highly hydrolyzed polyvinyl alcohol, so as to maintain said original shape of said hydrated implant, said method comprising: dehydrating said implant when the water content of said implant is within a range from about 30 to about 60 percent by weight under controlled conditions of relative humidity and temperature and time, wherein said relative humidity is at least about 80%, said drying temperature is within a range from about 10° to about 40° C., and said time of drying is at least two days and sufficient to enable said implant to be dried without distortion to a water content below about 30%, and said implant weighing between about 3 and about 10 grams and having a shape which is substantially similar to a human vertebral disc nucleus.

5. A method according to claim 4, wherein said drying temperature is within a range from about 20° to about 35° C. and wherein said relative humidity is within a range from about 90 to about 99%.

6. A method according to claim 5, wherein said relative humidity is at least 95% and wherein said time of drying is at least several days.

7. A method of producing a synthetic vertebral disc implant comprising highly hydrolyzed polyvinyl alcohol having a water content below about 30 weight percent and exhibiting (when viewed with no additional magnification beyond a naked eye) no visible distortion and no sharp edges, and having a minimum dehydrated volume, said method comprising: when said implant has a water content between about 30 to about 60 percent by weight, dehydrating said implant at a relative humidity of at least about 80%, at a drying temperature within a range from about 10° to about 40° C., and for a drying time which is at least two days.

8. A method according to claim 7, wherein said implant comprises highly hydrolyzed polyvinyl alcohol having a compressive strength of at least 4 MNm$^{-2}$, wherein said implant has a size within a range from about 3 to about 10 grams, and a shape which is substantially similar to a human vertebral disc nucleus wherein said relative humidity is within a range from about 90 to about 99%, and wherein said drying temperature is within a range from about 20° to about 35° C.

9. A method according to claim 8, wherein said implant weighs about 5 grams before dehydration, wherein said relative humidity is at least about 95%, and wherein said bulky hydrogel is PVA.

* * * * *